US00PP18384P3

(12) United States Plant Patent
Hanes

(10) Patent No.: US PP18,384 P3
(45) Date of Patent: Jan. 1, 2008

(54) ***VERBENA* PLANT NAMED 'RAP VIOTWO'**

(50) Latin Name: *Verbena hybrida*
Varietal Denomination: Rap Viotwo

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 105 days.

(21) Appl. No.: 11/371,671

(22) Filed: Mar. 10, 2006

(65) Prior Publication Data

US 2007/0214527 P1 Sep. 13, 2007

(51) Int. Cl.
*A01H 5/00* (2006.01)

(52) U.S. Cl. ..... Plt./308

(58) Field of Classification Search ..... Plt./308
See application file for complete search history.

(56) References Cited

PUBLICATIONS

PBR 05–4668, *Verbena*'Rap Viotwo', filed in Canada Mar. 29, 2005.*
PBR 20051908, *Verbena* 'Rap Viotwo', filed Nov. 14, 2005.*

* cited by examiner

*Primary Examiner*—Wendy C. Haas
*Assistant Examiner*—Georgia Helmer
(74) *Attorney, Agent, or Firm*—Jondle & Associates, P.C.

(57) ABSTRACT

A *verbena* plant particularly distinguished by deep violet-blue flowers that form a semi-spherical-shaped inflorescence, an early, continuous and abundant flowering response, medium green foliage with moderately dissected leaves, medium vigor, free-branching, and a moderately compact, partly spreading to decumbent and semi-trailing plant habit, is disclosed.

2 Drawing Sheets

Genus and species: *Verbena hybrida*
Variety denomination: 'Rap Viotwo'.

BACKGROUND OF THE NEW PLANT

The present invention comprises a new and distinct cultivar of *verbena,* botanically known as *Verbena hybrida* and hereinafter referred to by the cultivar name 'Rap Viotwo'. The new cultivar originated from a hybridization made in November 2001 in Gilroy, Calif. The female parent was '1281-1', a proprietary deep blue-flowered *verbena* plant (unpatented), while the male parent was '1252-4', a proprietary deep purple-flowered *verbena* plant (unpatented).

The new cultivar was created in November 2001 in Gilroy, Calif. and has been asexually reproduced repeatedly by vegetative cuttings and tissue culture in Gilroy, Calif. and Andijk, The Netherlands over a three-year period. A single plant was selected based on its desirable qualities. The plant has also been trialed at Gilroy, Calif. and Andijk, The Netherlands. The present invention has been found to retain its distinctive characteristics through successive asexual propagations.

Plant Breeder's Rights for this cultivar have been applied for in Canada on Mar. 29, 2005 and with the European Union on Oct. 14, 2005.

SUMMARY OF THE INVENTION

The following are the most outstanding and distinguishing characteristics of the new cultivar when grown under normal horticultural practices in Gilroy, Calif., and Hillscheid, Germany.

1. Deep violet-blue flowers and a semi-spherical-shaped inflorescence;

2. An early, continuous and an abundant flowering response;
3. Medium green foliage with moderately dissected leaves;
4. Medium vigor;
5. A free-branching and moderately compact plant habit; and
6. A partly spreading to decumbent and semi-trailing plant habit.

DESCRIPTION OF THE PHOTOGRAPHS

This new *verbena* plant is illustrated by the accompanying photographs which show overall plant habit including blooms, buds and foliage of the plant; the colors shown are as true as can be reasonably obtained by conventional photographic procedures. The photos are of an 11-week-old plant grown in a greenhouse in a Spring trial setting.

DESCRIPTION OF THE NEW CULTIVAR

Figure 1:
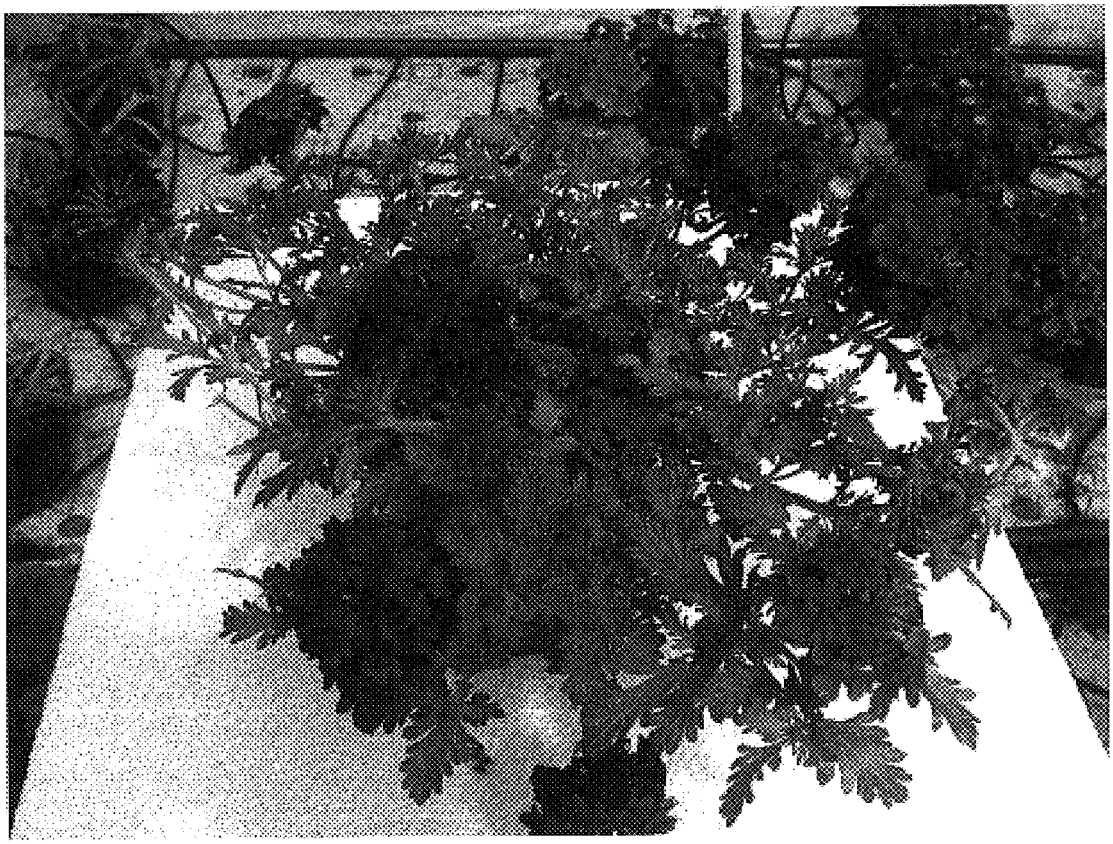
FIG. 1 shows the overall plant habit, including blooms, buds and foliage.
Figure 2:
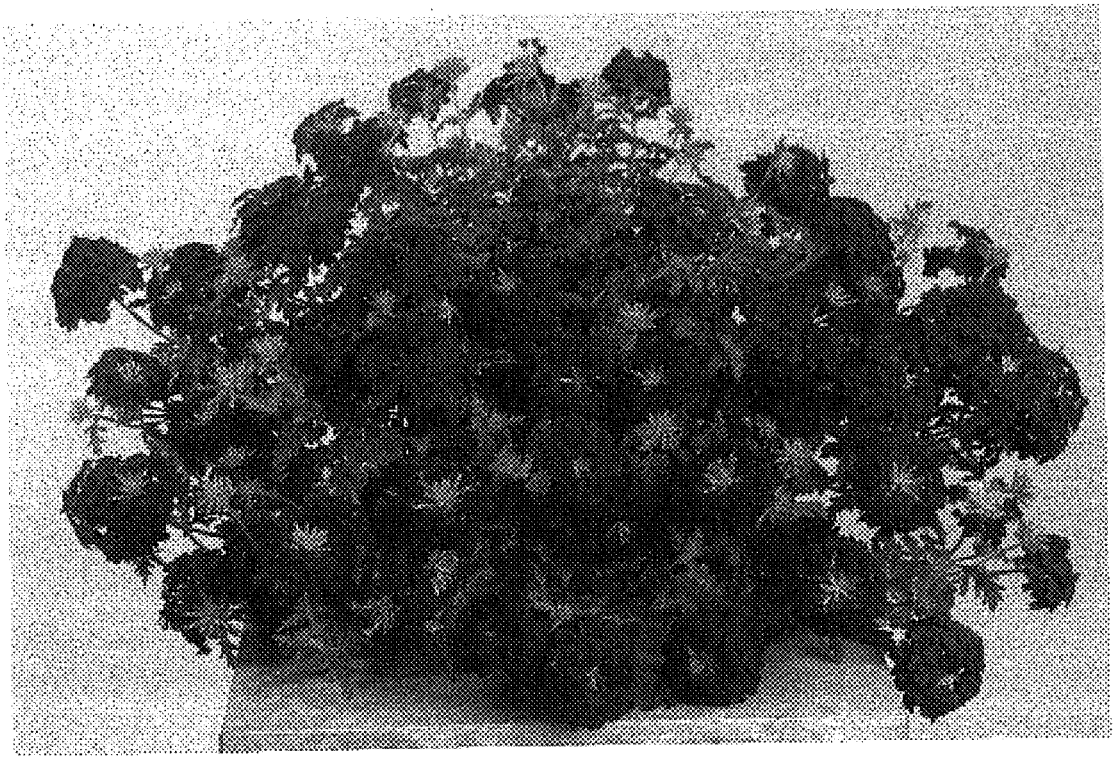
FIG. 2 shows the overall plant habit of the plant in a hanging basket.

The following detailed descriptions set forth the distinctive characteristics of 'Rap Viotwo'. The data which define these characteristics were collected from asexual reproductions carried out in Hillscheid, Germany. The plant history was taken on 11-week-old plants grown in a greenhouse in Hillscheid, Germany in Spring 2005. The plants were pinched once. Observations were made in mid-May 2005 when the plants were beginning to flower. Color readings were taken in the greenhouse in mid-May 2005 under natural light. Color references are primarily to The R.H.S. Colour Chart of The Royal Horticultural Society of London (R.H.S.) (2001 edition).

DETAILED BOTANICAL DESCRIPTION

Classification:

*Family.*—Verbenaceae.

*Botanical.*—*Verbena hybrida.*

*Common name.*—*Verbena.*

Parentage:

*Female parent.*—'1281-1', a proprietary (unpatented) deep blue-flowered *verbena* plant.

*Male parent.*—'1252-4', a proprietary (unpatented) deep purple-flowered *verbena* plant.

Growth:

*Form.*—Herbaceous annual.

*Growth and branching habit.*—Initially spreading and later decumbent to semi-trailing; relatively compact and free-branching.

*Height* (*measured from the top of the soil*).—15 cm.

*Width* (*horizontal plant diameter*).—35 cm.

*Time to produce a finished flowering plant.*—10 weeks for a 12-cm pot in the Spring.

*Outdoor plant performance.*—Use in containers and hanging baskets.

*Time to initiate and develop roots.*—Less than 14 days.

*Root description.*—Fibrous.

Stems:

*Number of branches per plant.*—18.

*Length.*—14 cm to 16 cm.

*Diameter* (*measured from the midpoint*).—0.3 cm.

*Internode length.*—1.5 cm to 2.5 cm.

*Color.*—RHS 143B.

*Anthocyanin.*—Absent.

*Texture.*—Finely pubescent.

Leaves:

*Arrangement.*—Opposite.

*Immature leaf.*—Color: Upper surface: RHS 137A. Lower surface: RHS 137C.

*Mature leaf.*—Color: Upper surface: RHS 137A. Lower surface: RHS 137C. Length: 2.0 cm to 2.5 cm. Width: 1.2 cm to 2.4 cm. Shape: Ovate with deep incisions. Apex: Obtuse to rounded. Base: Acute. Margin: Between pinnatifid to pinnatisect; incised (intermediate degree). Texture: Pilose hair; sparse on the upper surface and dense on the lower surface. Venation: Pinnate. Venation color: RHS 145A for the lower surface; the upper surface is indistinct.

*Petioles.*—Length: 0.3 cm to 0.6 cm. Diameter: 0.1 cm to 0.2 cm. Color: RHS 145A. Texture: Pubescent with relatively long and soft hair.

Flower buds:

*Shape.*—Cylindrical, tube-shaped.

*Length.*—Up to 1.1 cm.

*Diameter.*—0.2 cm to 0.25 cm.

*Color* (*at tight bud*).—RHS 92A (light violet-blue).

Inflorescence:

*Blooming habit.*—Flowers continuously from Spring through Fall; flowers appear about 9 to 10 weeks after planting of rooted cuttings.

*Lastingness of individual blooms on the plant.*—5 to 7 days.

*Fragrance.*—None.

*Inflorescence type.*—Mainly umbrella-shaped to semi-spherical; appears as umbels or corymbs, but actually is spikes.

*Horizontal diameter of inflorescence.*—4.5 cm.

*Vertical diameter of inflorescence.*—2 cm to 2.5 cm.

*Number of florets per inflorescence.*—15 to 25.

*Peduncle.*—Length: 3 cm to 5 cm. Diameter: 0.15 cm. Color: RHS 143C. Texture: Hispid, rough with hair and partly glandular hair.

Flowers:

*Floret form.*—Salver-shaped, formed by 5 petals that are partly fused and a long corolla tube.

*Floret diameter.*—1.3 cm to 1.5 cm.

*Immature flower.*—Color: Upper surface: RHS N89B. Lower surface: RHS 85A.

*Mature flower.*—Color: Upper surface: Mostly RHS N89B (deep violet-blue); some flowers may later become RHS 83B. Lower surface: RHS 85A (pale violet) and fading toward the center to RHS 85D. Corolla tube length: 1.6 cm to 1.9 cm. Corolla tube color: RHS 157A, white with a slight greenish hue.

*Petals.*—Length of lobe: 0.6 cm to 0.7 cm. Diameter of lobe: 0.5 cm to 0.6 cm. Lobe shape: Heart-shaped. Apex: Moderately emarginate. Base: Fused. Margin: Entire.

*Pedicels.*—Absent, florets are sessile.

*Calyx.*—General: 5 sepals forming a tube around the corolla base. Shape: Tube-shaped, furrowed. Length: 0.9 cm to 1.1 cm. Diameter: 0.2 cm to 0.3 cm. Color: RHS 143B (green). Apex: Acute (tiny tips). Base: Fused. Margin: No margin; fused nearly 100% of the length forming a tube. Texture: Dense short hair, glandular.

Reproductive organs:

*Stamens.*—4 near the opening of the corolla tube; the filaments appear fused with the corolla tube.

*Anther length.*—About 0.2 cm with two thecae.

*Pollen amount.*—Moderate.

*Pollen color.*—RHS 4C (light-yellow).

*Pistil.*—Has one style, about 1.0 cm to 1.2 cm in length.

Fruit/seed set: None observed.

Disease and insect resistance: Tolerant to powdery mildew.

COMPARISON WITH PARENTAL AND COMMERCIAL CULTIVARS

'Rap Viotwo' differs from the female parent '1281-1' (unpatented) in that 'Rap Viotwo' has a more violet flower color and is earlier to flower, while '1281-1' has a deep blue flower color. Additionally, 'Rap Viotwo' is tolerant to powdery mildew, while '1281-1' is not.

'Rap Viotwo' differs from the male parent '1252-4' (unpatented) in that 'Rap Viotwo' has a violet-blue flower color, while '1252-4' has a purple flower color. Additionally, 'Rap Viotwo' has a smaller plant habit, finer leaves and smaller inflorescences than '1252-4'.

'Rap Viotwo' differs from the commercial variety 'Tapien Violet' (unpatented) in that 'Rap Viotwo' has larger inflorescences and a deeper violet flower color than 'Tapien Violet'. Additionally, 'Rap Viotwo' has incised leaves, while 'Tapien Violet' has laciniate leaves.

'Rap Viotwo' differs from the commercial variety 'Rap Pur' (U.S. Plant Pat. No. 14,076) in that 'Rap Viotwo' has a violet-blue flower color, while 'Rap Pur' has a purple flower color. Additionally, 'Rap Viotwo' has a more free-branching and a finer plant structure than 'Rap Pur'.

I claim:

1. A new and distinct cultivar of *verbena* plant as shown and described herein.

* * * * *